United States Patent
Corbett, III et al.

(10) Patent No.: US 6,782,619 B2
(45) Date of Patent: Aug. 31, 2004

(54) METHOD OF MAKING HIGH CONTACT DENSITY ELECTRODE ARRAY

(75) Inventors: Scott S. Corbett, III, Portland, OR (US); Timothy J. Johnson, Kent, WA (US); Ben M. Clopton, Bainbridge Island, WA (US); Francis A. Spelman, Seattle, WA (US); Jeffery A. Strole, Ellensburg, WA (US); Joseph R. Ketterl, Seattle, WA (US)

(73) Assignee: Advanced Cochlear Systems, Inc., Snoqualmie, WA (US)

( * ) Notice: Subject to any disclaimer, the term of this patent is extended or adjusted under 35 U.S.C. 154(b) by 0 days.

(21) Appl. No.: 09/932,266

(22) Filed: Aug. 17, 2001

(65) Prior Publication Data

US 2003/0036790 A1 Feb. 20, 2003

(51) Int. Cl.$^7$ ............................ H01R 43/00; A61N 1/05
(52) U.S. Cl. ........................ 29/858; 264/295; 264/372; 264/263; 607/137
(58) Field of Search .................................. 264/104, 241, 264/272.12, 272.14, 272.16, 901, 904, 295, 263, 322; 607/55–57, 115–116, 118, 137, 125; 600/372–373, 377, 379; 29/825, 846–848, 858

(56) References Cited

U.S. PATENT DOCUMENTS

| | | | | |
|---|---|---|---|---|
| 4,686,765 A | * | 8/1987 | Byers et al. ............ | 264/272.15 |
| 4,762,135 A | * | 8/1988 | van der Puije et al. ...... | 607/116 |
| 5,720,099 A | | 2/1998 | Parker et al. ................. | 29/825 |
| 6,074,422 A | * | 6/2000 | Berrang et al. ............. | 607/137 |
| 6,374,143 B1 | * | 4/2002 | Berrang et al. ............. | 600/379 |

FOREIGN PATENT DOCUMENTS

WO     WO 01/12115 A1    2/2001

* cited by examiner

*Primary Examiner*—Kennedy Schaetzle
*Assistant Examiner*—Kristen Droesch
(74) *Attorney, Agent, or Firm*—Law Offices of Timothy E. Siegel; Timothy E. Siegel (57) ABSTRACT

A laminated multi-electrode biocompatible implant, comprising a first layer of flexible, biocompatible dielectric material having a first, exposed surface. A second layer of flexible biocompatible dielectric material, is adhered to the first layer. Further, a third layer of flexible biocompatible dielectric material is adhered to the second layer. Additionally, a first conductive trace is interposed between the first layer and the second layer and a second conductive trace interposed between said second layer and said third layer. Finally, a first conductor, which breaches said first layer, conductively connects the first conductive trace to the exposed surface of the first layer, thereby forming a first electrode and a second conductor, which breaches the first layer and the second layer, conductively connects the second conductive trace to the exposed surface of the first layer, thereby forming a second electrode.

13 Claims, 7 Drawing Sheets

METHOD OF MAKING HIGH CONTACT DENSITY ELECTRODE ARRAY

STATEMENT OF GOVERNMENT SUPPORT

The present invention was reduced to practice, in part, with government support under SBIR grant No. 1R43 DC 4614-01 awarded by the Small Business Research Program of the Department of Health and Human Services. The United States Government has certain rights in the invention.

BACKGROUND OF THE INVENTION

Today, there are many prospective applications for a high-density multi-electrode biocompatible implant. One of the most important is for a cochlear implant. The cochlea is a snail shaped organ of the inner ear that translates sound waves into electrical nerve impulses. A cochlear implant, by directly electrically stimulating the cochlea can effect hearing restoration in persons otherwise completely deaf and for whom other methods of hearing restoration would be ineffective. Compared to the cochlea, however, which includes approximately 30,000 receptive nerve endings, currently available cochlear implants are crude devices, capable of stimulating the cochlea with a degree of selectivity far beneath what the cochlea is capable of perceiving. Accordingly, in order to effect a more complete hearing restoration, cochlear implants having a higher density of precisely positioned electrodes are needed.

Because the cochlea has so many more sensing sites than an implant could possibly have electrodes, it is desirable to stimulate the cochlea at points between electrodes. This can be effected by "beam forming," in which neighboring electrodes are separately controlled to form a beam that has its maximum at a desired cochlear stimulation point. Unfortunately, in order to perform beam steering it is generally desirable to have electrodes that are spaced apart by no more than 100 to 150 um. Achieving this fine spacing of electrodes has proven a challenge to researchers.

The cochlea is not the only site within the body where a high-density implant could be of use, however. The brain, the retina and the heart are just a few other sites within the body where such an implant could be used. Unfortunately, providing such an implant proves to be quite difficult in practice.

Among the challenges encountered in the construction of an implant having a large number (>30) of closely spaced (<100 um) and precisely positioned electrodes is the problem of decomposition in the body due to attack by the body's interstitial fluid (ISF). Any seam in an implant will be attacked by ISF and may eventually come apart. Because of this, it is extremely important that biocompatible materials be used throughout an implant. Moreover, the more that an implant can take the form of a seamless, unitary whole the longer an implant can be expected to last within the body. This requirement conflicts with the greater level of complexity desired of implants.

Researchers at the University of Michigan have designed one type of probe that is currently in popular use. This probe is made by micro machining a silicon substrate using photolithographic techniques in order to achieve accurate positioning of closely spaced electrodes. Unfortunately the materials used are somewhat brittle. Accordingly this probe is not well suited for an application that requires flexure, such as a cochlear implant.

Additionally, multilayer printed circuit board (PCB) technology has advanced so that multilayer structures having traces on the order of microns thick are now available. There are a number of reasons, however, why this technology has, in general, not been applied to the biomedical arena. First, many of the materials used in PCB manufacture are not biocompatible, or degrade after implantation. Second, even flex circuits made from polyimide, a flexible dielectric, typically do not have the degree of flexibility necessary to facilitate the construction and placement of a cochlear implant.

Accordingly, there is a long-standing, unresolved need for a biocompatible, long-term implant that can precisely stimulate a sensory bodily organ, such as the cochlea.

SUMMARY OF THE INVENTION

In a first separate aspect the present invention is a laminated multi-electrode biocompatible implant, comprising a first layer of flexible, biocompatible dielectric material having a first, exposed surface. A second layer of flexible biocompatible dielectric material, is adhered to the first layer and, in turn, a third layer of flexible biocompatible dielectric material is adhered to the second layer. Additionally, a first conductive trace is interposed between the first layer and the second layer and a second conductive trace is interposed between the second layer and the third layer. Finally, a first inter-laminar conductor, which breaches the first layer, conductively connects the first conductive trace to the exposed surface of the first layer, thereby forming a first electrode and a second inter-laminar conductor, which breaches the first layer and the second layer conductively connects the second conductive trace to the exposed surface of the first layer, thereby forming a second electrode.

In a second separate aspect, the present invention is a method of making a biocompatible laminated multi-electrode implant, comprising providing a first lamina of flexible, biocompatible material and constructing a first set of conductive traces on the first lamina. A second lamina of flexible, biocompatible material is formed on top of the first lamina and the first set of conductive traces in such a manner that the second lamina adheres to the first lamina. Then, a second set of conductive traces is constructed on the second lamina. A third lamina of flexible, biocompatible material is formed on top of the second lamina and the second set of conductive traces in such a manner that the third lamina naturally adheres to the second lamina and has an exposed surface. A portion of the third lamina is removed to create a first opening, extending from the exposed surface to a first one of the second set of traces and a portion of the third lamina and the second lamina is removed to create a second opening, extending from the exposed surface to a first one of the second set of traces. Finally, conductive material is introduced into the first opening and the second opening, the conductive material extending through the entire length of the first opening and the second opening and thereby creating a first electrode and a second electrode on the exposed surface.

In a third separate aspect the present invention is a method of creating a bio-implant, having a preset shape, comprising the steps of creating a flexible structure having a set of conductors and electrodes that are connected to the conductors and thermo-forming the structure into the preset shape.

In a fourth separate aspect the present invention is a method of creating a cochlear implant, including the steps of creating a flat spiral structure having a proximal end, a plurality of electrode sites and a plurality of conductors leading from the electrode sites to the proximal end and expanding the flat, spiral structure into a three dimensional helix.

The foregoing and other objectives, features and advantages of the invention will be more readily understood upon consideration of the following detailed description of the invention, taken in conjunction with the accompanying drawings.

BRIEF DESCRIPTION OF THE DRAWINGS

FIG. 11 is a greatly expanded, cross-sectional view of the work piece of FIG. 10, taken along line A—A of FIG. 1, showing a prospective cut outline. In FIGS. 11–14 traces 18 are not shown, for ease of presentation.

FIG. 15b is a perspective view of a cochlear implant created by the mold of FIG. 15a.

DETAILED DESCRIPTION OF THE PREFERRED EMBODIMENT

Figure 1:
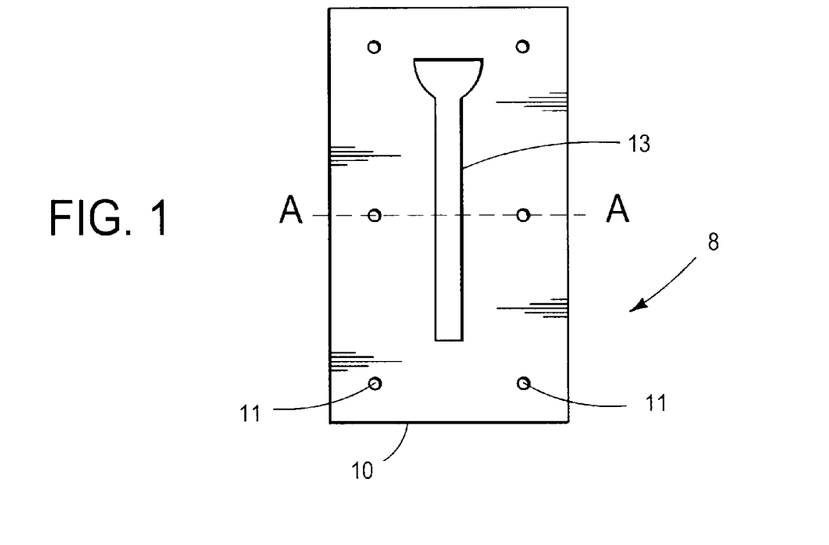
FIG. 1 is a plan view of a work piece set on a pin fixture and bearing the outline of a cochlear implant.
Figure 2:
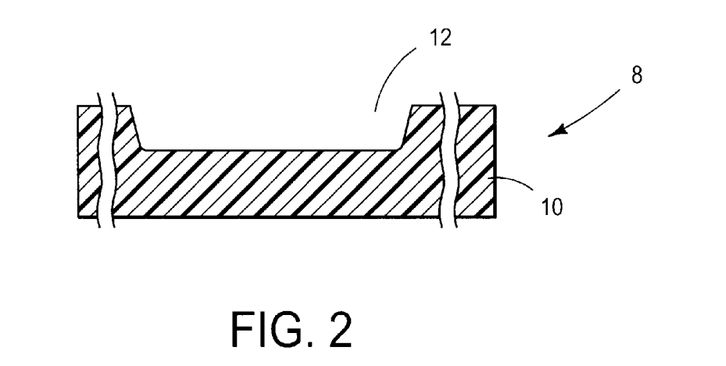
FIG. 2 is a greatly expanded cross-sectional view of a cochlear implant workpiece, taken along line A—A of FIG. 1, comprising a single sheet of material, having a depression formed in it.
Figure 3:
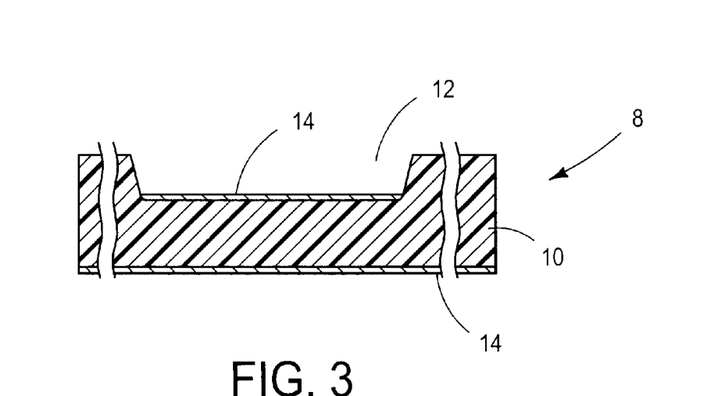
FIG. 3 is a greatly expanded cross-sectional view of the work piece of FIG. 1, taken along line A—A, at a further stage in the manufacturing process, in which conductive plating has been applied.

Referring to FIGS. 1 and 2, one preferred method of implementing the present invention begins with a work piece 8, originally including only a sheet 10 of liquid crystal polymer, that is up to 50.8 um (2 mil) thick. The sheet 10 is supported at a fixture by a set of pins 11. A cut outline 13, in the generalized shape of a cochlear implant is shown. Further similar sheets may be aligned and supported by the use of pins 11. A frequency multiplied ND:YAG laser is used to create a depression 12 in sheet 10. Next, (as shown in FIG. 3) layer 14 of conductive material such as gold, or a platinum-iridium alloy is deposited, typically by sputtering followed by electroplating, in depression 12 and onto the major surface of sheet 10 that is opposed to depression 12. The surfaces that are to be plated are first cleaned and roughened by means of plasma-etching. Areas in which the material of layer 14 is not desired may be protected from such deposition by means of a physical mask, or may be coated and then stripped by means of a laser or photolithography.

Figure 4:
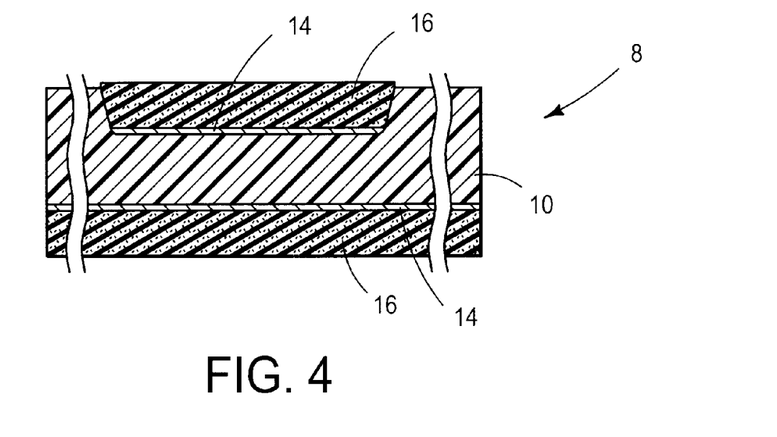
FIG. 4 is a greatly expanded cross-sectional view of the work piece of FIG. 1, taken along line A—A, at a further stage in the manufacturing process, in which photoresist has been applied.
Figure 5:
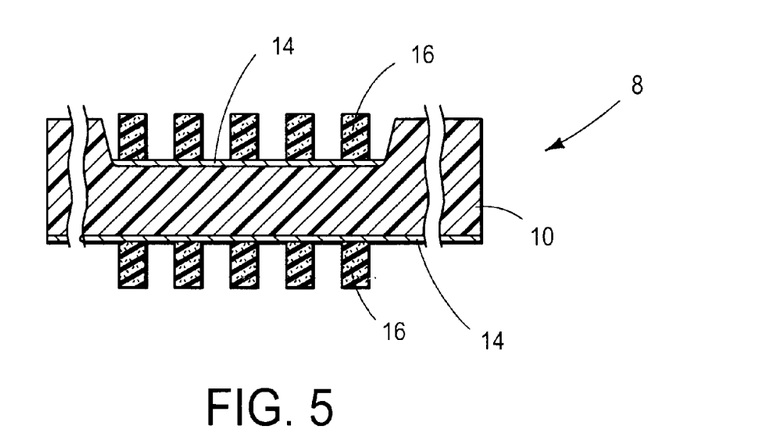
FIG. 5 is a greatly expanded cross-sectional view of the work piece of FIG. 1, taken along line A—A, at a further stage in the manufacturing process, in which the photoresist has been patterned.
Figure 6:
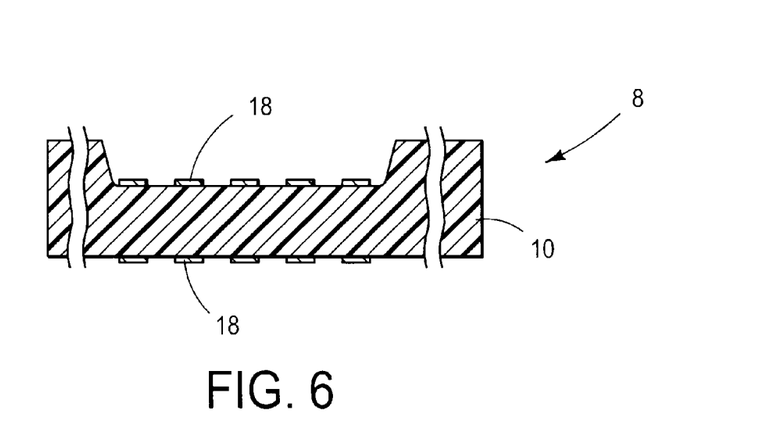
FIG. 6 is a greatly expanded cross-sectional view of the work piece of FIG. 1, taken along line A—A, at a further stage in the manufacturing process, in which the conductive plating has been patterned.

Referring to FIG. 4 a layer of photoresist 16 is applied over the conductive material. In FIG. 5 the photoresist 16 has been patterned by exposure to a masked light and/or a laser beam. FIG. 6 shows the resultant etching away of the gold 14 to form a pattern of traces 18.

In an alternative method the "lift off" process is used. In the lift off process a photomask is first applied (such as photoresist) which is patterned with a mask and UV light or with laser ablation or exposure. This is followed by deposition of the metal, followed by removal of the underlying mask, which "lifts off" the metal above it leaving traces where there was no photoresist underneath.

In yet another preferred method, an additive process is used where a thin deposit of metal is applied, typically by sputtering, followed by application and development of the photoresist mask. Additional metal is then electroplated, filling areas where the photoresist has been removed, followed by removal of the photoresist mask and final etching to remove residual base metal between traces.

Figure 7:
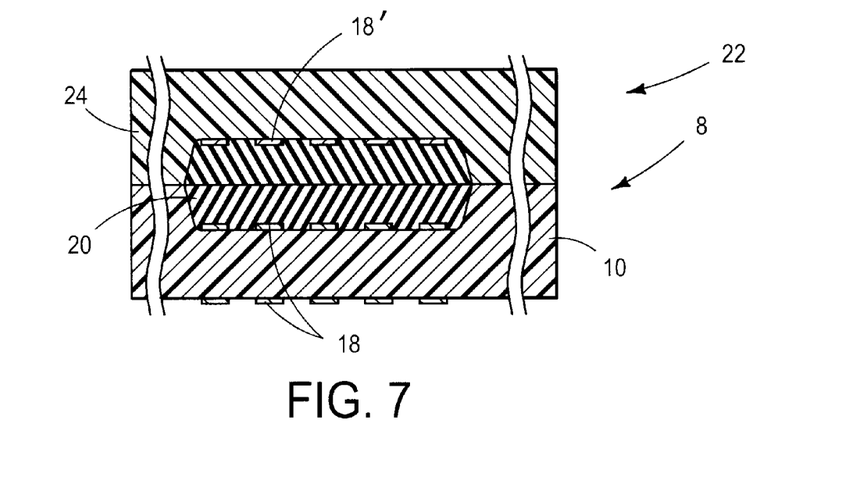
FIG. 7 is a greatly expanded cross-sectional view of the work piece of FIG. 1, taken along line A—A, at a further stage in the manufacturing process, in which an additional layer has been added.

In FIG. 7, depression 12 has been filled with an elastomer such as silicone 20. Additionally, a similarly constructed assembly 22, including an additional sheet of LCP 24 has been attached on top of sheet 10. Silicone, in general, naturally has adhesive qualities as well as good dielectric (insulation) properties. Moreover LCP sheets 10 and 24 may be cured or welded together, by application of heat and pressure.

Figure 8:
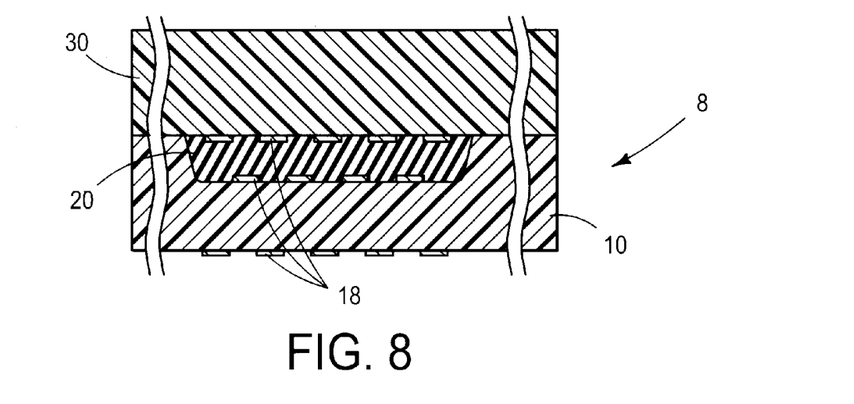
FIG. 8 is a greatly expanded cross-sectional view of the work piece of FIG. 1, taken along line A—A, at a further stage in the manufacturing process, in which an additional layer, alternative to that of FIG. 7, has been added.
Figure 9:
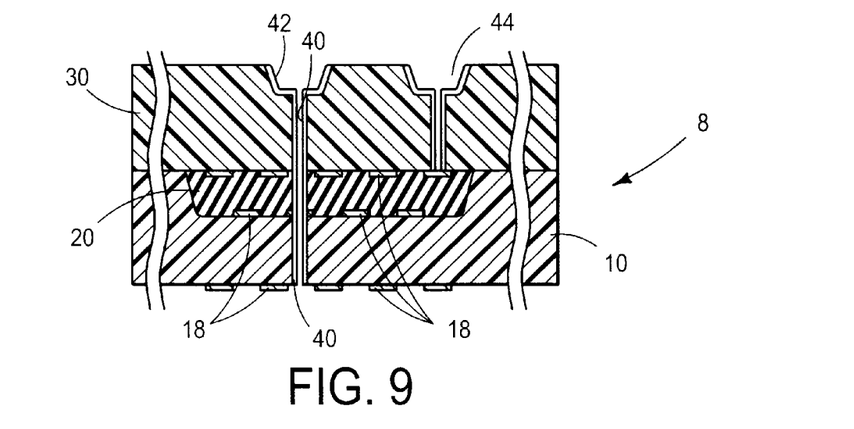
FIG. 9 is a greatly expanded, cross-sectional view of the work piece of FIG. 1, taken along line A—A, at a further stage in the manufacturing process, in which a plated via has been formed.

FIG. 8 shows an alternative scheme of lamination, in which an additional sheet of LCP 30 is adhered atop silicone 20. Top layer 30 may be treated in the exact same manner as sheet 10 to form another layer of circuitry. FIG. 9 shows the formation of a through via 40 to connect a trace 18 to the exterior of the work piece 8. In similar manner a blind via 44 connects a first layer trace 18 to the exterior. Through vias have the advantage that they are relatively easy to create, as there is no need to carefully monitor the depth that has been drilled. Additionally, they are easy to plate as fluids may pass entirely through the via, minimizing problems created by trapped air. Blind vias, which extend only to the feature of interest (in this instance trace 18) have the advantage that in a high density structure, they provide a freedom of design.

Note that if a through via was used in place of blind via 44, it would electrically connect two traces 18, which would be undesirable.

An indentation 42 has been machined in the vicinity of via 40. It may be an advantage for the electrodes to be recessed so that they do not touch the body tissue, which is somewhat conductive. By recessing the electrodes, large charge densities, which otherwise would appear at the outer edges of the electrode during stimulation of tissue, can be avoided. These charge densities, if present, would lead to potential electrode metal dissolution into the body.

Both via 40 and indentation 42 may be created by a laser, with gold then deposited by sputtering and built up by way of electroplating. Gold may be removed from undesired areas by means of laser ablating, or photolithography.

Figure 10:
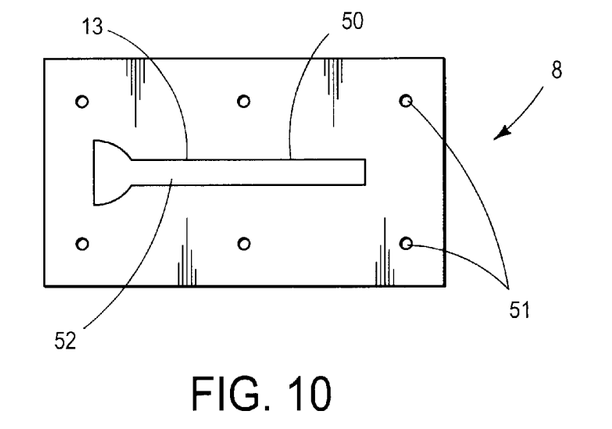
FIG. 10 is the same as FIG. 1.
Figure 11:
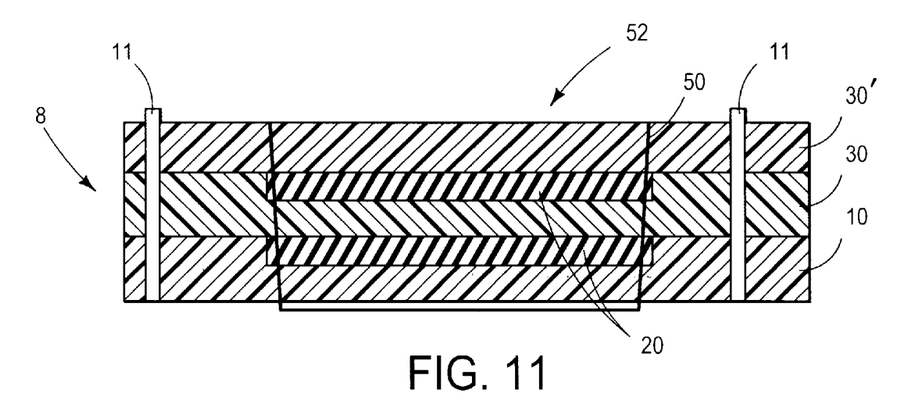
Figure 13:
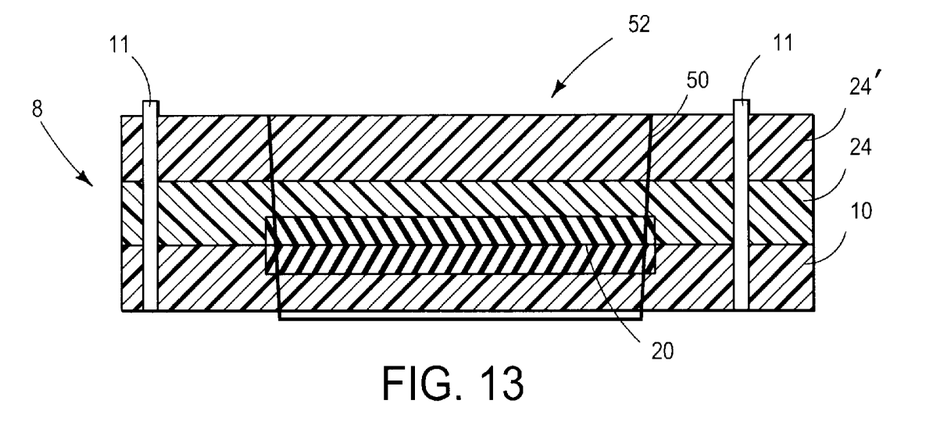
FIG. 13 is a greatly expanded, cross-sectional view of an alternative embodiment of the work piece of FIG. 11, taken along the same view-line, showing a prospective cut outline.

As shown in FIGS. 10, 11 and 13, a finished three dimensional structure 52 may then be cut away from the pin supported sheets of LCP (including additional sheet 30') by means of a laser, and in the general elongate shape of a cochlear implant, along a cut outline 13 (as noted previously).

Figure 12:
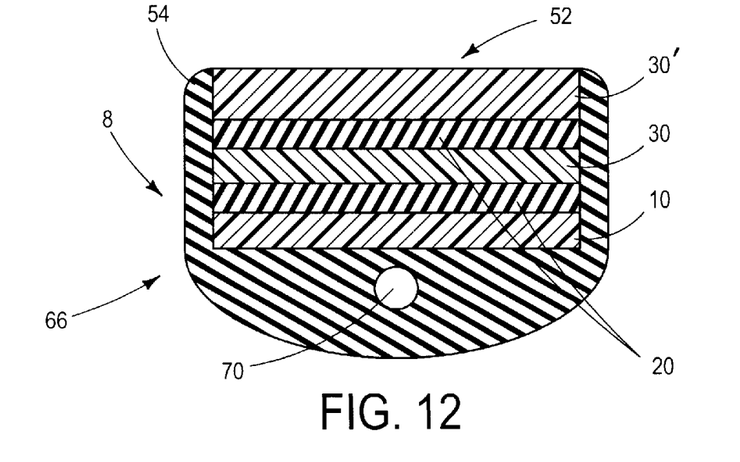
FIG. 12 is a greatly expanded, cross-sectional view of the cut out portion of the work piece of FIG. 1, taken along the line A—A, at a further stage in the manufacturing process, in which it has been set into a shell.
Figure 14:
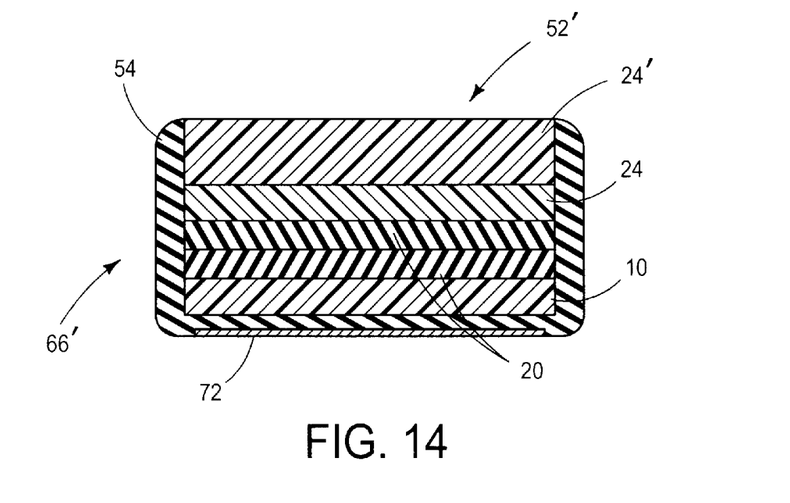
FIG. 14 is a greatly expanded, cross-sectional view of the work piece of FIG. 13, taken along the same view-line, at a further stage in the manufacturing process, in which it has been set into a shell.

FIGS. 13 and 14 shows the embodiment of FIG. 7 at the stage in the manufacturing process (having additional LCP sheet 24') that is the same as that of FIGS. 11 and 12 with respect to FIG. 8. FIGS. 11, 12, 13 and 14 do not show traces 18, for ease of presentation.

Figure 15A:
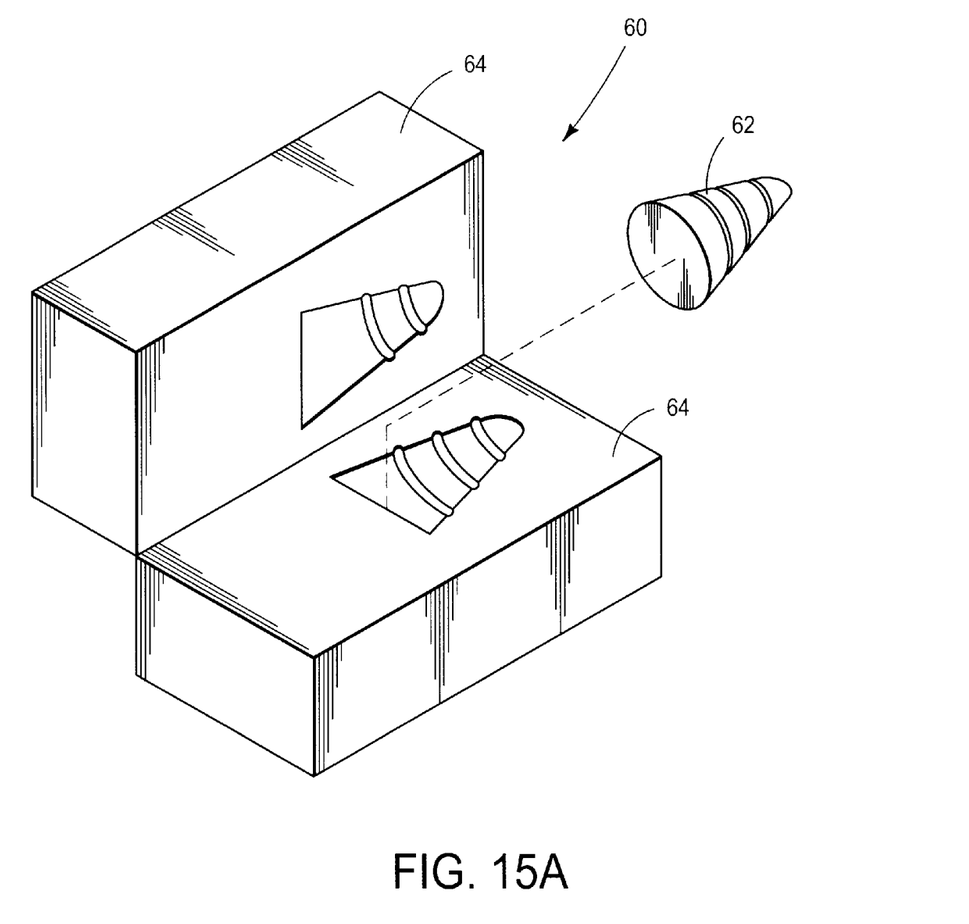
FIG. 15a is a perspective view of a mold for creating a cochlear implant, with enhanced in size electrodes for ease of presentation.

As shown in FIGS. 12, 14 and 15a, the cutout portion structure 52 may be molded into the shape of a cochlea. A three-part mold 60 such as that shown in FIG. 15 in which a center portion 62 in the shape of a cone defining a helix cooperates with a clam-shell structure 64, which receives the cut out portion 52 and an additional charge of liquid silicone which forms outer shell 54. This liquid silicone is available as a two part USP Class VI silicone from Nusil, Inc., which has an internet address of http://www.nusil.com. Alternatively, a one part USP Class VI silicone may be used.

Figure 15B:
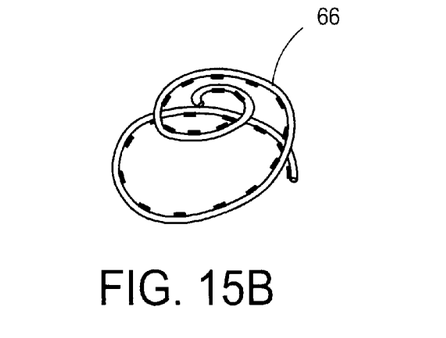

The result of this process is shown in FIGS. 12 and 15b as cochlear implant 66. FIG. 14 shows a variant cochlear implant 66'. FIG. 15b show larger than scale electrodes for ease of presentation. Separate molds are used for the left and right ear cochlear structure.

Because LCP is a thermo-plastic material, it can be reshaped after structure 52 is formed, and so it holds the helical form, together with outer shell 54, which is set in the mold shape. Because silicone is a thermo-set material the silicone layers 20 are held in the helical shape by the LCP layers, such as layer 10, and the outer shell 54. Any rearrangement of traces 18 caused by this process must not result in contact between any of the traces 18.

FIGS. 12 and 14 each show a cross section of molding of FIG. 15b, as made from the structures of FIGS. 11 and 13 respectively. In FIG. 12 a tube 70 has been set into the outer shell 54 to form a lumen. This facilitates the placement of cochlear implant 52 by permitting the introduction of a guide wire (not shown). It would also be possible to fill the tube 70 with shape memory material, thereby causing the implant to assume the shape of a cochlear at human body temperature. FIG. 14 shows a body of shape memory material 72, in the form of a strip, that is set to take the shape of a human cochlea at human body temperature.

In an alternative embodiment, the electrode traces are first patterned in a non-parallel manner such that after remolding into a helical shape, the traces become parallel. This permits the traces to be positioned prior to thermoforming in such a manner that the possibility that adjacent wires will contact each other after thermoforming is minimized.

In this application the term thermo-forming will include curing either a thermo-set material or a thermoplastic material or otherwise reforming a structure using heat and, possibly, the addition of thermo-set or thermoplastic material.

Figure 16A:
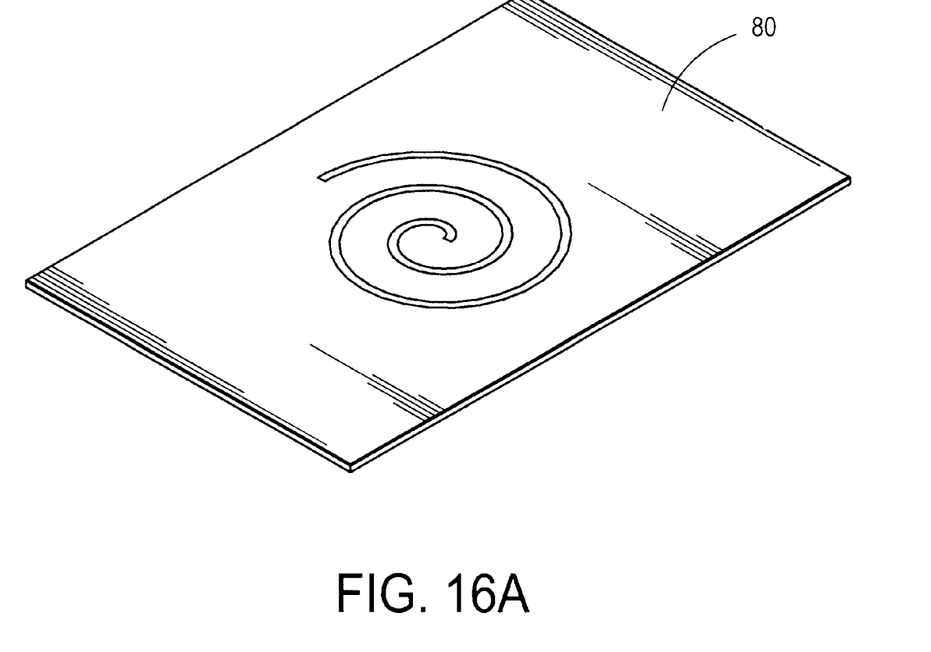
FIG. 16a is a perspective view of a substrate that has a spiral shape cut into it, according to a an alternative embodiment of the method of the present invention.
Figure 16B:
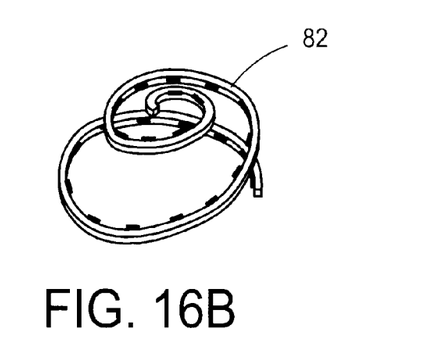
FIG. 16b is a perspective view of a cochlear implant made by the method of FIG. 16a, with enhanced in size electrodes for ease of presentation.

In an alternative embodiment shown in FIGS. 16a and 16b, a multilayer work piece 80 is built having traces that are in the form of a flat spiral. A spiral structure that includes these traces is severed from work piece 80 and expanded in the transverse dimension to form a cochlear implant 82.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method of creating a bio-implant in a helical shape adapted to conform to the helical shape of a mammalian cochlea interior volume, comprising the steps of:
   (a) providing a lamina of flexible, biocompatible material having a proximal end;
   b) constructing a set of conductive traces and a set of electrodes on said lamina and wherein each said conductive trace extends from said proximal end to a one of said electrodes, thereby creating a structure;
   (c) placing said structure into a mold that is in said helical shape of a mammalian cochlea interior volume;
   (d) adding a thermosetting material to said mold, together with said structure; and
   (e) thermo-forming said structure into said helical shape of a mammalian cochlea interior volume.

2. The method of claim 1 where at least a portion of said structure is made of thermo-plastic material.

3. A method of creating a bio-implant in a three-dimensional shape adapted to conform to the three-dimensional shape of an internal organ to be stimulated, comprising the steps of:
   a) creating a structure by:
      (i) providing a first lamina and second lamina of flexible biocompatible material each having a proximal end;
      (ii) constructing a first set of conductive traces on said first lamina and wherein each said conductive trace extends from said proximal end;
      (iii) constructing a second set of conductive traces on said second lamina and wherein each said conductive trace extends from said proximal end;
      (iv) attaching said second lamina and said second set of conductive traces on top of said first lamina and said first set of conductive traces in such a manner that said second lamina adheres to said first lamina;
      (v) attaching a third lamina of flexible biocompatible material on top of said second lam ma and said second set of conductive traces in such a manner that said third lamina adheres to said second lamina, said third lamina having an exposed surface;
      (vi) removing a portion of said third lamina to create a first opening, extending from said exposed surface to a first one of said second set of traces;
      (vii) removing a portion of said third lamina and said second lamina to create a second opening, extending from said exposed surface to a first one of said first set of traces; and
      (viii) introducing conductive material into said first opening and said second opening, said conductive material extending the entire length of said first opening and said second opening and thereby creating a first electrode and a second electrode on said exposed surface;

(b) placing said structure into a mold that is in said three-dimensional shape adapted to conform to the three-dimensional shape of an internal organ to be stimulated; and (c) thermo-forming said structure into said three-dimensional shape adapted to conform to the three-dimensional shape of an internal organ to be stimulated.

4. The method of claim 3 wherein sputtering is performed to deposit a layer of conductive material on said first lamina.

5. The method of claim 3 wherein electroplating is performed to thicken said layer of conductive material.

6. The method of claim 3 wherein said first set of traces is formed by way of photolithography.

7. The method of claim 3 wherein said step of removing a portion of said third lamina is performed by aiming a laser beam at the material to be removed.

8. The method of claim 3 wherein said step of introducing conductive material into said first opening and said second opening is performed by sputtering.

9. The method of claim 3 wherein said step of introducing conductive material into said first opening and said second opening is performed by electroplating.

10. The method of claim 3 wherein said first lamina is made of a liquid crystal polymer.

11. The method of claim 10 wherein said second lamina is made of silicone.

12. The method of claim 3 wherein said second lamina is formed by depositing liquefied silicone on said first lamina and first set of traces and curing said liquefied silicone in place on said first lamina.

13. The method of claim 3 wherein a portion of said first lamina is removed to form a depression, which is filled with material that is cured to form said second lamina.

* * * * *

UNITED STATES PATENT AND TRADEMARK OFFICE
CERTIFICATE OF CORRECTION

PATENT NO. : 6,782,619 B2  Page 1 of 1
DATED : August 31, 2004
INVENTOR(S) : Corbett, III et al.

It is certified that error appears in the above-identified patent and that said Letters Patent is hereby corrected as shown below:

<u>Column 6,</u>
Line 55, should read:
-- material on top of said second lamina and said --

Signed and Sealed this

Second Day of November, 2004

JON W. DUDAS
*Director of the United States Patent and Trademark Office*